United States Patent
Lebedev

(10) Patent No.: US 7,446,221 B1
(45) Date of Patent: Nov. 4, 2008

(54) PROCESS FOR MAKING TRICYCLODECENYL ESTERS

(75) Inventor: Mikhail Y. Lebedev, Jacksonville, FL (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 11/810,166

(22) Filed: Jun. 5, 2007

(51) Int. Cl.
*C07C 67/04* (2006.01)

(52) U.S. Cl. ...................................... 560/247

(58) Field of Classification Search ........................ None
See application file for complete search history.

(56) References Cited

U.S. PATENT DOCUMENTS

| 2,395,452 A | 2/1946 | Bruson ................... 260/497 |
| 2,814,639 A | 11/1957 | Bartlett et al. ............... 260/488 |
| 4,358,617 A | 11/1982 | Sprecker et al. ............. 568/373 |
| 4,453,000 A | 6/1984 | Schulte-Elte et al. ........ 560/256 |
| 4,522,977 A * | 6/1985 | Gardner ....................... 525/48 |
| 4,855,488 A | 8/1989 | Gude et al. ................. 560/249 |

FOREIGN PATENT DOCUMENTS

DE    3105399    10/1982

OTHER PUBLICATIONS

B. Wang et al., *Catal. Lett.* 96 (2004) 71.
*Zh. Org. Khim.* 31 (1995) 528.
*Neftek.* 37 (1997) 76.
E. Leitmannováet al., *Perf. Flav.* 29 (2004) 20.

* cited by examiner

*Primary Examiner*—Paul A Zucker
(74) *Attorney, Agent, or Firm*—Jonathan L. Schuchardt

(57) ABSTRACT

A practical, economical process for making tricyclodecenyl esters is disclosed. After reacting a lower carboxylic acid and a dicyclopentadiene in the presence of triflic acid to form the ester, the reaction mixture is distilled in the presence of a base to isolate a fragrance-quality tricyclodecenyl ester. Adding enough base to neutralize the triflic acid enables a distillation-only purification, facilitates starting material recovery, and avoids drawbacks of a basic workup.

20 Claims, No Drawings

PROCESS FOR MAKING TRICYCLODECENYL ESTERS

FIELD OF THE INVENTION

The invention relates to a process for making tricyclodecenyl esters. The esters derive from dicyclopentadiene compounds and are valuable fragrance components.

BACKGROUND OF THE INVENTION

Tricyclodecenyl esters, particularly the $C_2$-$C_4$ esters derived from dicyclopentadiene, are ubiquitous perfume ingredients found in detergents, shampoos, deodorants, hard-surface cleaners, and other applications. The most common tricyclodecenyl ester, which is made by reacting dicyclopentadiene with acetic acid, is tricyclodecenyl acetate or "TCDA." The product, which has a sweet, anise-like aroma, is marketed by several companies, including, for example, International Flavors & Fragrances (Cyclacet®), Quest (Jasmacyclene®), Millennium Specialty Chemicals (Navace™), and Symrise (Herbaflorat®).

Tricyclodecenyl esters are normally produced by acid-catalyzed addition of the corresponding carboxylic acids (acetic, propionic, butyric, isobutyric) to dicyclopentadiene (DCPD). A large excess of the carboxylic acid is typically used. Solvents, such as aromatic hydrocarbons, are often included. Many catalysts have been proposed, including perchloric acid (U.S. Pat. No. 2,814,639), sulfuric acid (U.S. Pat. No. 2,395,452), boron trifluoride and its addition complexes (U.S. Pat. Nos. 4,855,488 and 4,358,617), sulfamic acid (*Catal. Lett.* 96 (2004) 71), p-toluenesulfonic acid (*Zh. Org. Khim.* 31 (1995) 528 and *Neftek.* 37 (1997) 76), and perfluorinated acidic ion-exchange resins (DE 3,105,399).

U.S. Pat. No. 2,395,452 teaches to prepare TCDA using a 550% molar excess of acetic acid and dilute $H_2SO_4$ as the catalyst. More recently, Leitmannova et al. (*Perf. Flav.* 29 (2004) 20) optimized the sulfuric acid-catalyzed process and concluded that use of a 400% excess of acetic acid at 100° C. provides a favorable balance of product yield and reaction time. Unfortunately, however, acetic acid is relatively expensive and neutralization of the excess acid during workup generates a large amount of waste.

U.S. Pat. No. 4,855,488 teaches to prepare tricyclodecenyl esters from 93%-pure DCPD, a boron trifluoride catalyst, and at least a 200% molar excess of carboxylic acid. Instead of neutralizing the acid, the patentees teach to recover it using a costly stripping step. However, even distillation fails to provide a commercially acceptable product; therefore, the distilled material is further purified to remove traces of $BF_3$ catalyst and acetic acid by passing it through a column containing marble and/or activated carbon.

DE 3,619,797 teaches a process for obtaining TCDA using 1.1 to 5 molar excess of acetic acid and an ion-exchange resin. The water content is 0.5-15% based on the reactor charge, and acetic anhydride is added before distillative workup. In addition to the well-known drawbacks of ion-exchange resins (e.g., cost, loss of activity upon recycle), the need to charge acetic anhydride further complicates the method.

Commercial processes for making tricyclodecenyl esters typically require relatively pure dicyclopentadiene. The commercial grade DCPD material normally used is 93-94% DCPD, although a lower grade (83-88% pure) is available. High-purity DCPD (>98%) is also used. Unfortunately, esters made from the lower grade DCPD may not meet acceptable odor standards or isomer ratio requirements.

Conventional wisdom indicates that carboxylic acids (e.g., acetic acid) used to make tricyclodecenyl esters must also meet minimum purity standards. Crude acetic acid can be recovered from esterification processes used to make fragrance components, but this material is often contaminated with 20 wt. % or more of acetic anhydride, α-pinene, limonene, acetate esters, and other impurities. Because distillation of such streams is costly, they are often simply discarded.

Recently, as reported in copending application Ser. No. 11/489,100, filed Jul. 18, 2006, I described an improved way to make tricyclodecenyl esters that overcomes many of the drawbacks reported above. In that process, approximately equimolar amounts (0.8 to 1.3 molar ratio) of a $C_2$-$C_4$ carboxylic acid and a dicyclopentadiene react in the presence of triflic acid under conditions effective to produce the tricyclodecenyl ester. The process gives tricyclodecenyl esters in good yield from dicyclopentadienes while avoiding the need to use a large excess of the carboxylic acid. Moreover, fragrance-quality TCDA can be made from an inexpensive grade of DCPD and/or recycled acetic acid. Despite the advantages, there is room for improvement in how the esters are isolated. Although a large excess of carboxylic acid is not used, the typical workup still consists of adding a generous proportion of brine, water, and aqueous caustic to neutralize triflic acid and all of the excess, unreacted acetic acid. After separating phases, often with difficulty because of the tendency of the aqueous and organic layers to emulsify, the organic phase is distilled to isolate the tricyclodecenyl ester. Unfortunately, the basic workup does not permit recovery and reuse of any excess carboxylic acid. Moreover, the voluminous, salt-containing aqueous waste stream requires disposal and is preferably avoided. Sticky salts pose a reactor-cleanout challenge. Thus, issues created by the use of a basic workup are preferably avoided.

In sum, a simple, economical way to make tricyclodecenyl esters is needed. A valuable process would avoid the need to use a large excess of the carboxylic acid and would avoid the tradeoffs of using solvents, ion-exchange resins, or aqueous base workups. Ideally, the process would afford high yields of fragrance-quality tricyclodecenyl esters, even if the dicyclopentadiene and/or carboxylic acid sources are relatively impure.

SUMMARY OF THE INVENTION

The invention is a process for making tricyclodecenyl esters. The process comprises reacting approximately equimolar amounts of a $C_2$-$C_4$ carboxylic acid and a dicyclopentadiene in the presence of trifluoromethane-sulfonic acid (hereinafter "triflic acid") under conditions effective to produce the tricyclodecenyl ester. After forming the ester, the reaction mixture is distilled in the presence of a base to isolate the tricyclodecenyl ester.

I surprisingly found that by adding a small proportion of base, preferably just enough to neutralize the triflic acid, it is possible to use distillation to isolate tricyclodecenyl esters that are substantially free of unreacted carboxylic acid and dicyclopentadiene while avoiding drawbacks of the usual basic workup. The invention provides an easy, practical, and economical route to fragrance-quality tricyclodecenyl esters.

DETAILED DESCRIPTION OF THE INVENTION

In the inventive process, a $C_2$-$C_4$ carboxylic acid reacts with a dicyclopentadiene. Suitable carboxylic acids are aliphatic carboxylic acids having up to four carbons. Examples include acetic acid, propionic acid, butyric acid, and isobutyric acid. Higher carboxylic acids ($C_5$ and up) are excluded because the esters do not have much of an odor, while formic acid ($C_1$) gives esters with a less-desirable odor. Because they are readily available, acetic and propionic acids are most preferred.

While any desired grade of acetic acid can be used to make tricyclodecenyl acetates, I surprisingly found that crude acetic acid (80-95 wt. %, with a balance of organic compounds) can provide a fragrance-quality product. Acetic acid and acetic anhydride are staple reagents for the manufacture of esters used as fragrance components. Often, it is impractical to recover the acetic acid by conventional techniques such as extraction or distillation. Consequently, process streams containing acetic acid, acetic anhydride, and organic contaminants are commonplace in the fragrance industry. One such conveniently available stream contains about 80% acetic acid, 10-15% acetic anhydride, α-pinene, limonene, acetate esters, and other impurities. I found that this material can be used instead of glacial acetic acid (99% pure) in the inventive process to give a commercially acceptable tricyclodecenyl acetate (see Examples 1-2, below).

Suitable dicyclopentadienes have a carbon framework derived from dicyclopentadiene. The framework can be substituted with alkyl, halogen, aryl, or other groups that do not interfere with addition of the carboxylic acid to a carbon-carbon double bond of the dicyclopentadiene during preparation of the tricyclodecenyl ester. Preferred dicyclopentadienes are unsubstituted dicyclopentadiene (DCPD) and alkyl-substituted dicyclopentadienes such as the ones disclosed in U.S. Pat. Nos. 4,453,000 and 4,358,617, the teachings of which are incorporated herein by reference. DCPD is readily available and is most preferred.

The grade of the dicyclopentadiene used is not critical. In fact, this is an advantage of the inventive process because commercial grade DCPD (93-94% pure DCPD) or high-purity DCPD (>98%) is normally needed to achieve desirable fragrance character. Here, however, technical grade DCPD (e.g., >80% pure DCPD such as Lyondell Chemical Company's DCPD-101) can be used as a low-cost alternative with good results. Preferably, the dicyclopentadiene used has a purity within the range of 80 to 90%.

The carboxylic acid and the dicyclopentadiene are combined in roughly equimolar amounts. In particular, up to a thirty mole percent excess of the carboxylic acid can be used, or as little as eighty percent of a molar equivalent. Thus, the molar ratio of carboxylic acid to the dicyclopentadiene is within the range of 0.8 to 1.3. A preferred ratio is from 0.9 to 1.1; more preferred is a ratio within the range of 0.95 to 1.05. The ability to use equimolar amounts of the carboxylic acid and the dicyclopentadiene is another advantage of the invention. Using little or no excess carboxylic acid at the outset can reduce or eliminate the need for subsequent removal of the unreacted portion either by distillation or by neutralization and disposal of the resulting carboxylic acid salt. In contrast, prior-art methods typically require a large excess of the carboxylic acid.

Triflic acid catalyzes the addition reaction between the carboxylic acid and the dicyclopentadiene. The source of the triflic acid is not critical. It can be purchased, for example, from Aldrich Chemical and other suppliers. Only a catalytic amount of triflic acid is needed. Typically, the amount used will be less than 1 wt. % based on the amount of the dicyclopentadiene used. Preferably, less than 0.5 wt. % of triflic acid is used, more preferably less than 0.2 wt. %.

Catalysts other than triflic acid are generally not suitable for use. When boron trifluoride hydrate, for example, is used in the process of the invention, the tricyclodecenyl ester may meet specifications regarding desirable isomer proportions, but it fails to meet the requisite odor specification. Unlike acceptable commercial material, the product typically has a pungent, acidic note (see Comparative Examples 6 and 7, below).

The process is performed under conditions effective to produce tricyclodecenyl esters. "Tricyclodecenyl esters" are addition reaction products of one molar equivalent of a $C_2$-$C_4$ carboxylic acid and a dicyclopentadiene. The acid adds across one of the two carbon-carbon double bonds of the dicyclopentadiene. Each of the esters has a tricyclic ten-carbon framework that may have additional alkyl or other substituents that derive from the dicyclopentadiene. The tricyclodecenyl esters are normally generated as a mixture of two or more isomers, with one isomer often predominating. Preferably, the tricyclodecenyl ester derives from dicyclopentadiene. Thus, preferred tricyclodecenyl esters include, for example, tricyclodecenyl acetate (TCDA), tricyclodecenyl propionate (TCDP), tricyclodecenyl butyrate, and tricyclodecenyl isobutyrate.

Most preferably, the tricyclodecenyl ester is TCDA or TCDP. Following the reaction of acetic acid and DCPD to produce TCDA, distillation in the presence of base provides a TCDA-rich product. Commercially acceptable product comprises at least 95 wt. %, more preferably at least 98 wt. %, of TCDA isomers as measured by gas chromatography. The major isomer is preferably at least 90 wt. %, more preferably at least 92 wt. %, of the product. Preferably, the product also has a refractive index ($n_D^{20}$) within the range of 1.49 to 1.50, more preferably from 1.493 to 1.497. Preferred product has a relative density ($d_4^{20}$) within the range of 1.07 to 1.08, more preferably from 1.071 to 1.076.

To be commercially acceptable, the tricyclodecenyl esters usually must also satisfy well-recognized odor requirements. Relatively minor variations in isomer content may or may not impact commercial suitability. Moreover, a particular ester sample may have an acceptable isomers content but an unacceptable odor.

The tricyclodecenyl esters are easy to prepare. The dicyclopentadiene, triflic acid, and carboxylic acid are combined in any desired order. In a preferred approach, the dicyclopentadiene is added gradually to a well-agitated mixture of the carboxylic acid and triflic acid. See Examples 1, 2, 4, and 5.

While the reaction temperature is not critical, it is preferred to perform the reaction at a temperature within the range of 60° C. to 150° C., more preferably from 110° C. to 140° C. The reaction is normally complete within 1 to 10 hours, depending upon the conditions selected.

After the reaction is reasonably complete, the entire reaction mixture or a portion thereof is preferably transferred to a distillation vessel and combined with a relatively small proportion of base to effect a "partial neutralization" of the reaction mixture. Preferably, just enough base is used to neutralize the triflic acid. In other words, most or all of the unreacted carboxylic acid remains predominantly or exclusively in the free acid form. In particular, the amount of base used is 1 to 1.5 equivalents, preferably 1 to 1.1 equivalents, based on the amount of triflic acid used.

Suitable bases are compounds basic enough to accept a proton from triflic acid. Preferred bases are conjugate bases of acids having a $pK_a$ value greater than about minus 9. Because triflic acid is an exceptionally strong protic acid, many compounds that are not particularly basic will be suitable for use in practicing the process of the invention. For example, sodium chloride is a conjugate base of hydrogen chloride, which has a pKa=minus 7, so sodium chloride is a suitable base. Particularly preferred bases are ammonium, alkali metal, and alkaline earth metal hydroxides, oxides, alkoxides, carbonates, bicarbonates, carboxylates, phosphates, sulfates, nitrates, halides, and mixtures thereof. Specific examples include ammonium hydroxide, ammonium chloride, ammonium carbonate, sodium hydroxide, potassium hydroxide, lithium hydroxide, calcium carbonate, sodium bicarbonate, potassium bicarbonate, sodium acetate, sodium dihydrogen phosphate, sodium sulfate, sodium chloride, and the like. Caustic (50% aqueous NaOH) is a convenient choice.

The crude reaction mixture containing the tricyclodecenyl ester is distilled in the presence of the base to isolate a fragrance-quality ester product. Usually, most of the $C_2$-$C_4$ carboxylic acid is removed first, with pressure gradually reduced from >100 torr to <10 torr, preferably <5 torr, and more preferably about 1 torr. In a preferred approach, the distillation mixture is then set to reflux for 3-24 h, preferably 6-18 h, to remove remaining traces of the carboxylic acid. Distillation of the remaining material, preferably at <5 torr, and particularly at <1 torr, provides commercial-grade tricyclodecenyl esters (see Examples 1 and 2, below). Usually, a center cut containing material having an acceptable boiling range is isolated.

Any unreacted dicyclopentadiene or carboxylic acid can be recovered by distillation and reused in a subsequent reaction to make additional tricyclodecenyl ester. This contrasts with processes that use a conventional basic workup to remove unreacted carboxylic acid; in such processes, a salt of the carboxylic acid is usually lost in a large volume of aqueous waste. Other drawbacks of processes requiring an extractive workup are discussed above in the Background section.

As noted previously, an advantage of the invention is the ability to use a relatively impure $C_2$-$C_4$ carboxylic acid source. As Example 1 shows, a by-product stream containing 76 wt. % acetic acid, 18 wt. % acetic anhydride, and a balance of terpene impurities can be used successfully to make a fragrance-quality TCDA. Enough water is added to hydrolyze the acetic anhydride and triflic acid is added. The progress of hydrolysis is followed by any convenient means, such as gas chromatography. When most or all of the acetic anhydride has been hydrolyzed, the carboxylic acid stream is conveniently reacted with the dicyclopentadiene in the presence of the triflic acid used for hydrolysis.

The process of the invention can be practiced in any desired mode. Thus, a batch, semi-continuous, or continuous process can be employed.

The following examples merely illustrate the invention. Those skilled in the art will recognize many variations that are within the spirit of the invention and scope of the claims.

EXAMPLE 1

TCDA Synthesis

First Reaction in a Series

A. Acetic Anhydride Hydrolysis. A by-product stream (515 g) containing acetic acid (76 wt. %), acetic anhydride (18 wt. %), α-pinene, limonene, acetate esters, and other impurities, is combined with enough water (16.4 g) to hydrolyze the acetic anhydride. Triflic acid (1.36 g) is added, and the mixture is heated with stirring to 110° C. Gas chromatography (GC) analysis of the resulting dark-brown mixture indicates the absence of acetic anhydride, about 90 wt. % of acetic acid, and the balance of a complex mixture of organic compounds.

B. Synthesis of TCDA. Dicyclopentadiene ("DCPD," 1048 g, 86% pure) is added dropwise at 115-120° C. to the mixture obtained in Step A over 4 h. The reaction mixture stirs for an additional 2 h at 130° C. and is then cooled to 40° C. Crude material (1564 g) is distilled with aqueous sodium hydroxide (1.0 g of 50% solution) added to the distillation pot. Acetic acid (100 g) is first stripped off at 150 to 1 torr (i.e., 150 to 1 mm Hg). The distillation column is then set for 12 h of total reflux at 1 torr to remove residual acetic acid. Distillation of the remaining material at 1 torr provides commercial-grade TCDA (911 g, 68% based on DCPD). Major isomer by GC: 92.9%; Isomer A: 1.8%; Isomer B: 4.2%; Isomer C, 0.55%.

Targeted ranges for TCDA: Major isomer: >90%; Isomer A: <2%; Isomer B: 1-6%; Isomer C: <3%.

EXAMPLE 2

TCDA Synthesis

Consecutive Reaction

A. Acetic Anhydride Hydrolysis. Recycled acetic acid (100 g) from Example 1 and more of the same by-product stream (415 g) used in Example 1 are combined with enough water (13.2 g) to hydrolyze the acetic anhydride. Triflic acid (1.36 g) is added, and the mixture is heated with stirring to 110° C. GC analysis of the resulting dark-brown mixture indicates the absence of acetic anhydride, about 90 wt. % of acetic acid, and the balance of a complex mixture of organic compounds.

B. Synthesis of TCDA. DCPD (1048 g, 86% pure) is added dropwise at 115-120° C. to the mixture obtained in Step A over 4 h. The reaction mixture is stirred for an additional 2 h at 130° C. and is then cooled to 40° C. Crude material (1564 g) is distilled with 0.86 g of 50% aqueous NaOH added to the distillation pot. Acetic acid (100 g) is removed at 150-1 torr. The distillation column is then set for 12 h of total reflux at 1 torr to remove residual acetic acid. Distillation of remaining material at 1 torr provides commercial-grade TCDA (947 g, 71% based on DCPD). Major isomer by GC: 92.9%; Isomer A: 1.6%; Isomer B: 4.3%; Isomer C, 0.5%.

COMPARATIVE EXAMPLE 3

Distillation without Neutralization of Triflic Acid

The procedure of Example 1 is repeated, except that no NaOH solution is added to the distillation pot in Step B. Distillation of the crude reaction mixture (1554 g) provides acetic acid (145 g) and TCDA (670 g, only 47% based on DCPD) that does not meet isomer ratio specifications required for commercial product. Major isomer by GC: 93.1%; Isomer A: 2.5% (too high); Isomer B: 3.0%; Isomer C, 0.67%.

EXAMPLE 4

Tricyclodecenyl Propionate (TCDP) Synthesis

First Reaction in a Series

DCPD (970 g, 86% pure) is added dropwise at 110-120° C. to a mixture of fresh propionic acid (530 g) and triflic acid (1.27 g) over 3.5 h. The reaction mixture stirs for an additional 1.5 h at 120-125° C. and is then cooled to 40° C. Crude material (1499 g) is distilled with aqueous sodium hydroxide (1.08 g of 50% solution) added to the distillation pot. Propionic acid (103 g) is first removed at 150 to 1 torr. The distillation column is then set for 20 h of total reflux at 1 torr to remove residual propionic acid. Distillation of remaining material at 1 torr provides commercial-grade TCDP (852 g, 69% based on DCPD). Major isomer by GC: 93.1%; Isomer A: 1.4%; Isomer B: 4.3%; Isomer C: 0.46%; Isomer D: 0.16%.

Targeted ranges for TCDP: Major isomer: >90%; Isomer A: <2.5%; Isomer B: 2-5%; Isomer C: <3%; Isomer D: <1%.

EXAMPLE 5

TCDP Synthesis

Consecutive Reaction

DCPD (970 g, 86% pure) is added dropwise at 125-130° C. to a mixture of recycled propionic acid (103 g) from Example 4, fresh propionic acid (440 g), and triflic acid (1.27 g) over 3.5 h. The reaction mixture stirs for an additional 1.5 h at 130-135° C. and is then cooled to 40° C. Crude material (1511 g) is distilled with aqueous sodium hydroxide (0.95 g of 50% solution) added to the distillation pot. Propionic acid (120 g) is first removed at 150 to 1 torr. The distillation column is then set for 20 h of total reflux at 1 torr to remove residual propionic acid. Distillation of remaining material at 1 torr provides commercial-grade TCDP (848 g, 68% based on DCPD). Major isomer by GC: 92.7%; Isomer A: 1.6%; Isomer B: 4.2%; Isomer C, 0.5%; Isomer D: 0.16%.

COMPARATIVE EXAMPLE 6

$BF_3.2H_2O$ Catalyst

A. Acetic Anhydride Hydrolysis. A by-product stream (600 g) containing acetic acid (91.2 wt. %), acetic anhydride (2.6 wt. %), α-pinene, limonene, acetate esters, and other impurities, is combined with enough water (1.07 g) to hydrolyze the acetic anhydride. Boron trifluoride dihydrate complex (4.85 g of 96% pure material) is added, and the mixture is heated with stirring to 110° C. Gas chromatography (GC) analysis of the resulting dark-brown mixture indicates the absence of acetic anhydride, about 90 wt. % of acetic acid, and the balance of a complex mixture of organic compounds.

B. Synthesis of TCDA. DCPD (1048 g, 86% pure) is added dropwise at 115-140° C. to the mixture obtained in Step A over 3 h. The reaction mixture stirs for an additional 3 h at 140° C. and is then cooled to 40° C. Crude material is distilled with aqueous sodium hydroxide (7.0 g of 50% solution) added to the distillation pot. Acetic acid is first stripped off at 20 torr. The distillation column is then set for 20 h of total reflux at 1 torr to remove residual acetic acid. The remaining material is distilled at 1 torr. The resulting TCDA product (708 g, 73% based on DCPD) meets target specifications regarding isomer content (major isomer by GC: 92.0%; Isomer A: 1.2%; Isomer B: 5.5%; Isomer C, 1.1%). However, the product fails the odor specification because it has a pungent, acidic odor.

COMPARATIVE EXAMPLE 7

$BF_3.2H_2O$ Catalyst

The procedure of Comparative Example 6 is generally followed, except that 31.0 g of 50% aqueous sodium hydroxide solution (not 7.0 g) is added to the distillation pot in Part B. The resulting TCDA product (441 g, 34% based on DCPD) meets target specifications regarding isomer content (major isomer by GC: 91.7%; Isomer A: 1.4%; Isomer B: 5.6%; Isomer C, 1.1%). However, the product fails the odor specification because it has a pungent, acidic odor.

Comparative Examples 6 and 7 show that it is important to use triflic acid to catalyze the addition of the carboxylic acid to the dicyclopentadiene according to the process of the invention because even with partial neutralization, the boron trifluoride catalyst fails to provide a product having acceptable odor. As is discussed in copending application Ser. No. 11/489,100, commercially acceptable TCDA can be made using a $BF_3$ catalyst if a large excess of acetic acid and DCPD having a purity of 93+% are used; in that case, the material is isolated by distillation but without partial neutralization.

The examples are meant only as illustrations. The following claims define the invention.

I claim:

1. A process comprising: (a) reacting a $C_2$-$C_4$ carboxylic acid and a dicyclopentadiene at a carboxylic acid:dicyclopentadiene molar ratio within the range of 0.8 to 1.3 in the presence of triflic acid to produce a tricyclodecenyl ester; and (b) distilling the reaction mixture in the presence of 1 to 1.5 equivalents, based on the amount of triflic acid, of a base to isolate the tricyclodecenyl ester from unreacted dicyclopentadiene and unreacted carboxylic acid.

2. The process of claim 1 wherein the unreacted dicyclopentadiene, unreacted $C_2$-$C_4$ carboxylic acid, or both are recovered and used in a subsequent reaction to make additional tricyclodecenyl ester.

3. The process of claim 1 wherein at least a portion of the $C_2$-$C_4$ carboxylic acid is generated by hydrolyzing an acyclic anhydride corresponding to the $C_2$-$C_4$ carboxylic acid with water in the presence of triflic acid.

4. The process of claim 1 wherein the distillation is performed in the presence of 1.0 to 1.1 equivalents of the base.

5. The process of claim 1 wherein the base is selected from the group consisting of ammonium, alkali metal, and alkaline earth metal hydroxides, oxides, alkoxides, carbonates, bicarbonates, carboxylates, phosphates, sulfates, nitrates, halides, and mixtures thereof.

6. The process of claim 1 wherein the dicyclopentadiene is unsubstituted dicyclopentadiene (DCPD).

7. The process of claim 6 wherein the dicyclopentadiene has a purity within the range of 80 to 90%.

8. The process of claim 1 wherein the distilled tricyclodecenyl ester is a commercially acceptable fragrance component.

9. The process of claim 1 wherein the $C_2$-$C_4$ carboxylic acid is selected from the group consisting of acetic, propionic, n-butyric, and isobutyric acids.

10. The process of claim 1 wherein the $C_2$-$C_4$ carboxylic acid is acetic acid, the dicyclopentadiene is DCPD, and the tricyclodecenyl ester is tricyclodecenyl acetate (TCDA).

11. The process of claim 10 wherein the DCPD is added gradually to a mixture comprising acetic acid and triflic acid.

12. The process of claim 10 wherein the distilled tricyclodecenyl ester comprises at least 95 wt. % of TCDA isomers.

13. The process of claim 12 wherein the distilled ester comprises at least 98 wt. % of TCDA isomers.

14. The process of claim 12 wherein the distilled ester has an index of refraction ($n_D^{20}$) within the range of 1.49 to 1.50.

15. The process of claim 12 wherein the distilled ester has a relative density ($d_4^{20}$) within the range of 1.07 to 1.08.

16. The process of claim 1 wherein the carboxylic acid:dicyclopentadiene molar ratio is within the range of 0.9 to 1.1.

17. The process of claim 1 wherein the amount of triflic acid is less than 1 wt. % based on the amount of the dicyclopentadiene.

18. The process of claim 1 wherein the reaction is performed at a temperature within the range of 60° C. to 150° C.

19. The process of claim 1 wherein the reaction is performed at a temperature within the range of 110° C. to 140° C.

20. The process of claim 1 performed in batch, semi-continuous, or continuous mode.

* * * * *

UNITED STATES PATENT AND TRADEMARK OFFICE
CERTIFICATE OF CORRECTION

PATENT NO. : 7,446,221 B1 Page 1 of 1
APPLICATION NO. : 11/810166
DATED : November 4, 2008
INVENTOR(S) : Mikhail Y. Lebedev It is certified that error appears in the above-identified patent and that said Letters Patent is hereby corrected as shown below:

On the Title Page, Item (73), the correct Assignee should read as follows:

--Millennium Specialty Chemicals, Inc.--

Signed and Sealed this

Twentieth Day of January, 2009

JON W. DUDAS
*Director of the United States Patent and Trademark Office*